United States Patent [19]

Hasegawa

[11] Patent Number: 4,895,835
[45] Date of Patent: Jan. 23, 1990

[54] MURAMYL PEPTIDE DERIVATIVES AND USE THEREOF

[75] Inventor: Akira Hasegawa, Gifu, Japan

[73] Assignee: Nisshin Oil Mills, Ltd., Tokyo, Japan

[21] Appl. No.: 272,496

[22] Filed: Nov. 17, 1988

[30] Foreign Application Priority Data

Nov. 20, 1987 [JP] Japan ............................. 62-293281

[51] Int. Cl.$^4$ .................. A61K 37/02; C07K 9/00
[52] U.S. Cl. .................................. 514/8; 530/322; 424/88; 424/89
[58] Field of Search .............. 530/322; 514/8; 424/88, 424/89

[56] References Cited

U.S. PATENT DOCUMENTS

| | | | |
|---|---|---|---|
| 4,101,536 | 7/1978 | Yamamura et al. | 530/322 |
| 4,315,913 | 2/1982 | Durette | 514/8 |
| 4,323,559 | 4/1982 | Audibert et al. | 514/8 |
| 4,430,265 | 2/1984 | Yamamura et al. | 530/322 |
| 4,780,313 | 10/1988 | Koichiro et al. | 514/8 |

FOREIGN PATENT DOCUMENTS

| | | | |
|---|---|---|---|
| 58-172399 | 11/1983 | Japan | 514/8 |
| 59-20297 | 1/1984 | Japan | 514/8 |
| 61-275299 | 5/1986 | Japan | 514/8 |

OTHER PUBLICATIONS

Kotani et al., Yakugaku Zasshi, *Immunopharmacological Activities of Bacterial Cell Walls and Related Synthetic Compounds* (Muramyl Peptides), 103(1), pp. 1–27 (1983).

Derguini et al., *A Versatile Synthesis of Retinoids Via Condensation of the Side–Chain to Cyclic Ketones,* Tetrahedron Letters, 51, pp. 4899–4902 (1979).

Matsumoto et al., *Anti–Infectious Activity of the Synthetic Muramyl Dipeptide Analogue MDP-Lys (L18),* "Immunostimulants", pp. 79–97, Japan Sci. Soc. Press, Tokyo, 1987.

*Primary Examiner*—Lester L. Lee
*Attorney, Agent, or Firm*—Bryan, Cave, McPheeters & McRoberts

[57] ABSTRACT

Muramyl peptide derivatives having the formula (I)

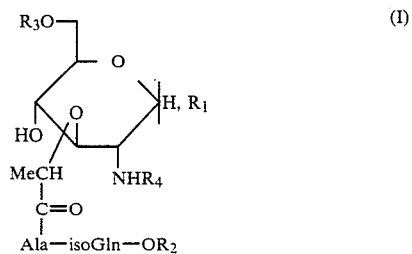

wherein $R_3$ is a long chain acyloxyacyl group, $R_1$ is hydrogen or hydroxy mercapto, acyloxy or acylthio group, $R_2$ is hydrogen or alkyl group and $R_4$ is acyl, which are useful as immunomodulators.

17 Claims, No Drawings

MURAMYL PEPTIDE DERIVATIVES AND USE THEREOF

BACKGROUND OF THE INVENTION (1) Field of the Invention

This invention relates to novel muramyl peptide derivatives. The muramyl peptide derivatives can act on immunological mechanisms(especially on cells relevant to immune responses)in the living body of mammals including human being and are useful as immunomodulators.

(2) Description of the Prior Art

It is known that muramyl peptides possess a wide variety of biological activities.

As their in vitro activities, there are (a) activity on cells relevant to immune response (e.g., monocytes and macrophages, B lymphocytes, T lymphocytes, natural killer cells or the like); (b) activity on other cells (e.g., thrombocytes, fibroblasts, osteoclasts or the like); (c) activation of complementary system and so forth. As in vivo activities, there are (a) modulation of immune responses; (b) increase of natural resistance against microbial infections and tumor development, and so forth [see S. Kotani and H. Takada: Immunopharmacological activities of bacterial cell walls and related synthetic compounds (muramyl peptides), YAKUGAKU ZASSHI, 103(1), pp1 - 27(1983)]. Known muramyl peptides are e.g., B30-muramyl dipeptide [S. Kusumoto et al, Tetrahedron Lett. 49, pp4899-4902(1978)], muramyl dipeptidelysin (K. Matsumoto et al., Immunostimulants, Now and Tomorrow p79-97, Japan Sci. Soc. Press, Tokyo, 1987), and those disclosed in Japanese patent unexamined publication Nos. -172399, 59-20297 and 61-275299.

There is still need for other compounds having excellent activities than known muramyl peptide derivatives.

SUMMARY OF THE INVENTION

According to this invention, it provides a muramyl peptide derivative of the formula (I):

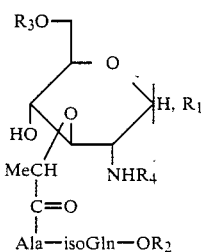

in which "Ala" is

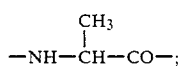

"iso-Gln" is

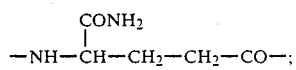

$R_1$ is hydrogen atom, hydroxy group, mercapto group, a $C_{2-20}$alkanoyloxy group, a $C_{2-20}$alkanoylthio group, $R_3O-$ or $R_3S-$; $R_2$ is hydrogen atom or a $C_{1-20}$alkyl group, $R_3$ is a group of the sub-formula:

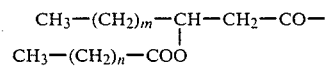

(n is an integer of 10-14 and m is an integer of 8-12); $R_4$ is a $C_{2-4}$alkanoyl group.

It also provides an immunomodulator comprising the muramyl peptide derivative of the formula (I) and a pharmaceutically acceptable carrier.

PREFERRED EMBODIMENTS OF THE INVENTION

In the definitions of the formula (I), examples of the $C_{2-20}$alkanoyloxy group or $C_{2-20}$alkanoylthio group in $R_1$ are acetoxy, acetylthio, propionyloxy, propionylthio, butyryloxy, butyrylthio, valeryloxy, valerylthio, iso-valeryloxy, isovalerylthio, pentanoyloxy, pentanoylthio, pivaloyloxy, pivaloylthio, heptanoyloxy, heptanoylthio, octanoyloxy, octanoylthio, nonanoyloxy, nonanoylthio, decanoyloxy, decanoylthio, undecanoyloxy, undecanoylthio, dodecanoyloxy, dodecanoylthio, tridecanoyloxy, tridecanoylthio, tetradecanoyloxy, tetradecanoylthio, pentadecanoyloxy, pentadecanoylthio, hexadecanoyloxy, hexadecanoylthio, heptadecanoyloxy, heptadecanoylthio, octadecanoyloxy, octadecanoylthio, nonadecanoyloxy, nonadecanoylthio, eicosayloxy and eicosaylthio. The preferred one is tetradecanoyloxy or tetradecanoylthio.

Examples of the $C_{1-20}$alkyl group in $R_2$ are methyl, ethyl, propyl, butyl, pentyl, hexyl, octyl, nonyl, decanyl, undecanyl, dodecanyl, tridecanyl, tetradecanyl, pentadecanyl, hexadecanyl, heptadecanyl, octadecanyl, nonadecanyl and eicosanyl.

Examples of the group of the sub-formula:

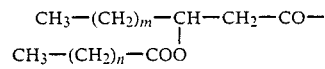

and 3-dodecanoyloxydodecanoyl, 3-tridecanoyloxydodecanoyl, 3-tetradecanoyloxydodecanoyl, 3-hexadecanoyloxydodecanoyl, 3-pentadecanoyloxydodecanyl, 3-dodecanoyloxytridecanoyl, 3-tridecanoyloxytridecanoyl, 3-tetradecanoyloxytridecanoyl, 3-pentadecanoyloxytridecanoyl, 3-hexadecanoyloxytridecanoyl, 3-dodecanoyloxytetradecanoyl, 3-tridecanoyloxytetradecanoyl, 3-tetradecanoyloxytetradecanoyl, 3-pentadecanoyloxytridecanoyl, 3-hexadecanoyloxytetradecanoyl, 3-dodecanoyloxypentadecanoyl, 3-tridecanoyloxypentadecanoyl, 3-tetradecanoyloxypentadecanoyl, 3-pentadecanoyloxypentadecanoyl, 3-hexadecanoyloxypentadecanoyl, 3-dodecanoyloxyhexadecanoyl, 3-tridecanoyloxyhexadecanoyl, 3-tetradodecanoyloxyhexadecanoyl, 3-pentadecanoyloxyhexadecanoyl and 3-hexadodecanoyloxyhexadecanoyl. Among such acyloxyacyl groups, 3-hexadecanoyloxytetradecanoyl, 3-tetradecanoyloxytetradecanoyl and 3-dodecanoyloxytetradecanoyl are preferable.

Examples of the $C_{2-4}$alkanoyl group in $R_4$ are acetyl, propionyl butyryl and isobutyryl, among which acetyl is preferable.

$R_1$ is preferred to be hydrogen or hydroxy.
$R_2$ is preferred to be hydrogen or methyl.

"Ala" is preferred to be a residue of L-alanine and "iso-Gln" is preferred to be a residue derived from D-isoglutamine.

The compounds of the formula (I) in the invention are basically derivatives of muramyl dipeptide, and hence the muramyl dipeptide moiety is desirously to be that having the same configuration as in natural muramyl dipeptide. That is, the muramic acid moiety is D-configuration and the dipeptide moiety is L-alanine-D-isoglutamine. However, muramyl dipeptides having other configurations which may exist are included in this invention.

The acyloxyacyl group in $R_3$ possesses one asymmetric carbon atom and may be D-form, L-form or mixture thereof.

Further, the compound of the formula (I) of $R_2$ being hydrogen atom contains one carboxyl group, which may form a pharmaceutically acceptable salt (e.g., an alkalimetal salt such as sodium or potassium salt). Such salt is also included in this invention.

Specifically, interesting compounds according to this invention may be mentioned as follows.

N-[[2-O-{2-acetamido-2,3-dideoxy-6-O-[(3R)-3-dodecanoyloxydodecanoyl]-D-glucopyranos-3-yl}-D-lactoyl]]-L-alanyl-D-isoglutamine methyl ester, N-[[2-O-{2-acetamido-2 3-dideoxy-6-O-[(3R)-3-tetradecanoyloxydodecanoyl]-D-glucopyranos-3-yl}-D-lactoyl]]-L-alanyl-D-isoglutamine methyl ester, N-[[2-O-{2-acetamido-2,3-dideoxy-6-O-[(3R)-3-hexadecanoyloxydodecanoyl]-D-glucopyranos-3-yl}-D-lactoyl]]-L-alanyl-D-isoglutamine methyl ester, N-[[2-O-{2-acetamido-2,3-dideoxy-6-O-[(3R)-3-dodecanoyloxytetradecanoyl]-D-glucopyranos-3-yl}-D-lactoyl]]-L-alanyl-D-isoglutamine methyl ester, N-[[2-O-{2-acetamido-2,3-dideoxy-6-O-[(3R)-3-tetradecanoyloxytetradecanoyl]-D-glucopyranos-3-yl}-D-lactoyl]]-L-alanyl-D-isoglutamine methyl ester, N-[[2-O-{2-acetamido-2,3-dideoxy-6-O-[(3R)-3-hexadecanoyloxytetradecanoyl]-D-glucopyranos-3-yl}-D-lactoyl]]-L-alanyl-D-isoglutamine methyl ester, N-[[2-O-{2-acetamido-2,3-dideoxy-6-O-[(3R)-3-dodecanoyloxyhexadecanoyl]-D-glucopyranos-3-yl}-D-lactoyl]]-L-alanyl-D-isoglutamine methyl ester, N-[[2-O-{2-acetamido-2,3-dideoxy-6-O-[(3R)-3-tetradecanoyloxyhexadecanoyl]-D-glucopyranos-3-yl}-D-lactoyl]]-L-alanyl-D-isoglutamine methyl ester, N-[[2-O-{2-acetamido-2,3-dideoxy-6-O-[(3R)-3-hexadecanoyloxyhexadecanoyl]-D-glucopyranos-3-yl}-D-lactoyl]]-L-alanyl-D-isoglutamine methyl ester, N-[[2-O-{2-acetamido-1,5-anhydro-2,3-dideoxy-6-O-[(3R)-3-dodecanoyloxydodecanoyl]-D-glucitol-3-yl}-D-lactoyl]]-L-alanyl-D-isoglutamine methyl ester, N-[[2-O-{2-acetamido-1,5-anhydro-2 3-dideoxy-6-O[(3R)-3-tetradecanoyloxydodecanoyl]-D-glucitol-3-yl}-D-lactoyl]]-L-alanyl-D-isoglutamine methyl ester, N-[[2-O-{2-acetamido-1,5-anhydro-2 3-dideoxy-6-O[(3R)-3-hexadecanoyloxydodecanoyl]-D-glucitol-3-yl}-D-lactoyl]]-L-alanyl-D-isoglutamine methyl ester, N-[[2-O-{2-acetamido-1,5-anhydro-2,3-dideoxy-6-O[(3R)-3-dodecanoyloxytetradecanoyl]-D-glucitol-3-yl}-D-lactoyl]]-L-alanyl-D-isoglutamine methyl ester, N-[[2-O-{2-acetamido-1,5-anhydro-2,3-dideoxy-6-O[(3R)-3-tetradecanoyloxytetradecanoyl]-D-glucitol-3-yl}-D-lactoyl]]-L-alanyl-D-isoglutamine methyl ester, N-[[2-O-{2-acetamido-1,5-anhydro-2,3-dideoxy-6-O[(3R)-3-hexadecanoyloxytetradecanoyl]-D-glucitol-3-yl}-D-lactoyl]]-L-alanyl-D-isoglutamine methyl ester, N-[[2-O-{2-acetamido-1,5-anhydro-2,3-dideoxy-6-O[(3R)-3-dodecanoyloxyhexadecanoyl]-D-glucitol-3-yl}-D-lactoyl]]-L-alanyl-D-isoglutamine methyl ester, N-[[2-O-{2-acetamido-1,5-anhydro-2,3-dideoxy-6-O[(3R)-3-tetradecanoyloxyhexadecanoyl]-D-glucitol-3-yl}-D-lactoyl]]-L-alanyl-D-isoglutamine methyl ester, N-[[2-O-{2 -acetamido-1,5-anhydro-2,3-dideoxy-6-O-[(3R)-3-hexadecanoyloxyhexadecanoyl]-D-glucitol-3-yl}-D-lactoyl]]-L-alanyl-D-isoglutamine methyl ester, N-[[2-O-{2-acetamido-2,3-dideoxy-6-O-[(3R)-3-dodecanoyloxydodecanoyl]-1-thio-β-D-glucopyranos-3-yl}-D-lactoyl]]-L-alanyl-D-isoglutamine methyl ester, N-[[2-O-{2-acetamido-2,3-dideoxy-6-O-[(3R)-3-tetradecanoyloxydodecanoyl]-1-thio-β-D-glucopyranos-3-yl}-D-lactoyl]]-L-alanyl-D-isoglutamine methyl ester, N-[[2-O-{2-acetamido-2,3-dideoxy-6-O-[(3R)-3-hexadecanoyloxydodecanoyl]-1-thio-β-D-glucopyranos-3-yl}-D-lactoyl]]-L-alanyl-D-isoglutamine methyl ester, N-[[2-O-{2-acetamido-2,3-dideoxy-6-O-[(3R)-3-dodecanoyloxytetradecanoyl]-1-thio-β-D-glucopyranos-3-yl}-D-lactoyl]]-L-alanyl-D-isoglutamine methyl ester, N-[[2-O-{2-acetamido-2,3-dideoxy-6-O-[(3R)-3-tetradecanoyloxytetradecanoyl]-1-thio-β-D-glucopyranos-3-yl}-D-lactoyl]]-L-alanyl-D-isoglutamine methyl ester, N-[[2-O-{2-acetamido-2,3-dideoxy-6-O-[(3R)-3-hexadecanoyloxytetradecanoyl]-1-thio-β-D-glucopyranos-3-yl}-D-lactoyl]]-L-alanyl-D-isoglutamine methyl ester, N-[[2-O-{2-acetamido-2,3-dideoxy-6-O-[(3R)-3-dodecanoyloxyhexadecanoyl]-1-thio-β-D-glucopyranos-3-yl}-D-lactoyl]]-L-alanyl-D-isoglutamine methyl ester, N-[[2-O-{2-acetamido-2,3-dideoxy-6-O-[(3R)-3-tetradecanoyloxyhexadecanoyl]-1-thio-β-D-glucopyranos-3-yl}-D-lactoyl]]-L-alanyl-D-isoglutamine methyl ester, N-[[2-O-{2-acetamido-2,3-dideoxy-6-O-[(3R)-3-hexadecanoyloxyhexadecanoyl]-1-thio-β-D-glucopyranos-3-yl}-D-lactoyl]]-L-alanyl-D-isoglutamine methyl ester, N-[[2-O-{2-acetamido-1,5-anhydro-2,3-dideoxy-6-O-[(3R)-3-dodecanoyloxydodecanoyl]-D-glucitol-3-yl}-D-lactoyl]]-L-alanyl-D-isoglutamine, N-[[2-O-{2-acetamido-1,5-anhydro-2,3-dideoxy-6-O-[(3R)-3-tetradecanoyloxydodecanoyl]-D-glucitol-3-yl}-D-lactoyl]]-L-alanyl-D-isoglutamine, N-[[2-O-{2-acetamido-1,5-anhydro-2,3-dideoxy-6-O-[(3R)-3-hexadecanoyloxydodecanoyl]-D-glucitol-3-yl}-D-lactoyl}]-L-alanyl-D-isoglutamine, N-[[2-O-{2-acetamido-1,5-anhydro-2,3-dideoxy-6-O-[(3R)-3-dodecanoyloxytetradecanoyl]-D-glucitol-3-yl}-D-lactoyl]]-L-alanyl-D-isoglutamine, N-[[2-O-{2-acetamido-1,5-anhydro-2,3-dideoxy-6-O-[(3R)-3-tetradecanoyloxytetradecanoyl]-D-glucitol-3-yl}-D-lactoyl]]-L-alanyl-D-isoglutamine, N-[[2-O-{2-acetamido-1,5-anhydro-2,3-dideoxy-6-O-[(3R)-3-hexadecanoyloxytetradecanoyl]-D-glucitol-3-yl}-D-lactoyl]]-L-alanyl-D-isoglutamine, N-[[2-O-{2-acetamido-1,5-anhydro-2,3-dideoxy-6-O-[(3R)-3-dodecanoyloxyhexadecanoyl]-D-glucitol-3-yl}-D-lactoyl]]-L-alanyl-D-isoglutamine, N-[[2-O-{2-acetamido-1,5-anhydro-2,3-dideoxy-6-O-[(3R)-3-tetradecanoyloxyhexadecanoyl]-D-glucitol-3-yl}-D-lactoyl]]-L-alanyl-D-isoglutamine, N-[[2-O-{2-acetamido-1,5-anhydro-2,3-dideoxy-6-O-[(3R)-3-hexadecanoyloxyhexadecanoyl]-D-glucitol-3-yl}-D-lactoyl]]-L-alanyl-D-isoglutamine, N-[[2-O-{2-acetamido-2,3-dideoxy-6-O-[(3R)-3-dodecanoyloxydodecanoyl]-D-glucopyranos-3-yl}-D-lactoyl]]-L-alanyl-D-isoglutamine, N-[[2-O-{2-acetamido-2,3-dideoxy-6-O-[(3R)-3-tetradecanoyloxydodecanoyl]-D-glucopyranos-3-yl}-D-lactoyl]]-L-alanyl-D-isoglutamine, N-[[2-O-{2-acetamido-2,3-dideoxy-6-O-[(3R)-3-hexadecanoyloxydodecanoyl]-D-glucopyranos-3-yl}-D-lactoyl]]-L-alanyl-D-isoglutamine, N-[[2-O-{2-acetamido-2,3-dideoxy-6-O-[(3R)-3-dodecanoyloxytetradecanoyl]-D-glucopyranos-3-yl}-D-lactoyl]]-L-alanyl-D-isoglutamine, N-[[2-O-{2-acetamido-2,3-dideoxy-6-O-[(3R)-3-tetradecanoyloxytetradecanoyl]-D-glucopyranos-3-yl}-D-lactoyl]]-L-alanyl-D-isoglutamine, N-[[2-O-{2-acetamido-2,3-dideoxy-6-O-[(3R)-3-hexacanoyloxytetradecanoyl]-D-glucopyranos-3-yl}-D-lactoyl]]-L-alanyl-D-isoglutamine, N-[[2-O-{2-acetamido-2,3-dideoxy-6-O-[(3R)-3-dodecadecanoyloxyhexadecanoyl]-D-glucopyranos-3-yl}-D-lactoyl]]-L-alanyl-D-isoglutamine, N-[[2-O-{2-acetamido-2,3-dideoxy-6-O-[(3R)-tetradecanoyloxyhexadecanoyl]-D-glucopyranos-3-yl}-D-lactoyl]]-L-alanyl-D-isoglutamine, N-[[2-O-{2-acetamido-2,3-dideoxy-6-O-[(3R)-3-hexadecanoyloxyhexadecanoyl]-D-glucopyranos-3-yl}-D-lactoyl]]-L-alanyl-D-isoglutamine, N-[[2-O-{2-acetamido-2,3-dideoxy-6-O-[(3R)-3-dodecanoyloxdodecanoyl]-1-thio-8-D-glucopyranos-3-yl}-D-lactoyl]]-L-alanyl-D-isoglutamine, N-[[2-O-{2-acetamido-2,3-dideoxy-6-O-[(3R)-3-tetradecanoyloxydodecanoyl]-1-thio-8-D-glucopyranos-3-yl}-D-lactoyl]]-L-alanyl-D-isoglutamine, N-[[2-O-{2-acetamido-2,3-dideoxy-6-O-[(3R)-3-hexadecanoyloxydodecanoyl]-1-thio-8-D-glucopyranos-3-yl}-D-lactoyl]]-L-alanyl-D-isoglutamine, N-[[2-O-{2-acetamido-2,3-dideoxy-6-O-[(3R)-3-dodecanoyloxytetradecanoyl]-1-thio-8-D-glucopyranos-3-yl}-D-lactoyl]]-L-alanyl-D-isoglutamine, N-[[2-O-{2-acetamido-2,3-dideoxy-6-O-[(3R)-3-tetradecanoyloxytetradecanoyl]-1-thio-8-D-glucopyranos-3-yl}-D-lactoyl]]-L-alanyl-D-isoglutamine, N-[[2-O-{2-acetamido-2,3-dideoxy-6-O-[(3R)-3-hexadecanoyloxytetradecanoyl]-1-thio-8-D-glucopyranos-3-yl}-D-lactoyl]]-L-alanyl-D-isoglutamine, N-[[2-O-{2-acetamido-2,3-dideoxy-6-O-[(3R)-3-dodecanoyloxyhexadecanoyl]-1-thio-8-D-glucopyranos-3-yl}-D-lactoyl]]-L-alanyl-D-isoglutamine, N-[[2-O-{2-acetamido-2,3-dideoxy-6-O-(3R)-3-tetradecanoyloxyhexadecanoyl]-1-thio-8-D-glucopyranos-3-yl}-D-lactoyl]]-L-alanyl-D-isoglutamine, N-[[2-O-{2-acetamido-2,3-dideoxy-6-O-[(3R)-3-hexadecanoyloxyhexadecanoyl]-1-thio-8-D-glucopyranos-3-yl}-D-lactoyl]]-L-alanyl-D-isoglutamine, N-[[2-O-{1-O-tetradecanoyl-2-acetamido-2,3-dideoxy-6-O-[(3R)-3-dodecanoyloxytetradecanoyl]-D-glucopyranos-3yl}-D-lactoyl]]-L-alanyl-D-isoglutamine methyl ester, N-[[2-O-{1-O-tetradecanoyl-2-acetamido-2,3-dideoxy-6-O-[(3R)-3-tetradecanoyloxytetradecanoyl]-D-glucopyranos-3yl}-D-lactoyl]]-L-alanyl-D-isoglutamine methyl ester, N-[[2-O-{1-O-tetradecanoyl-2-acetamido-2,3-dideoxy-6-O-[(3R)-3-hexadecanoyloxytetradecanoyl]-D-glucopyranos-3-yl}-D-lactoyl]]-L-alanyl-D-isoglutamine methyl ester, N-[[2-O-{1-O-tetradecanoyl-2-acetamido-2 3-dideoxy-6-O-[(3R)-3-dodecanoyloxytetradecanoyl]-D-glucopyranos-3-yl}-D-lactoyl]]-L-alanyl-D-isoglutamine N-[[2-O-{1-O-tetradecanoyl-2-acetamido-2,3-dideoxy-6-O-[(3R)-3-tetradecanoyloxytetradecanoyl]-D-glucopyranos-3-yl}-D-lactoyl]]-L-alanyl-D-isoglutamine N-[[2-O-{1-O-tetradecanoyl-2-acetamido-2 3-dideoxy-6-O-[(3R)-3-hexadecanoyloxytetradecanoyl]-D-glucopyranos-3-yl}-D-lactoyl]]-L-alanyl-D-isoglutamine and N-[[2-O-{1-O-[(3R)-3-hexadecanoyloxytetradecanoyl]-2-acetamido-2,3-dideoxy-6-O-[(3R)-3-hexadecanoyloxytetradecanoyl]-D-glucopyranos-3-yl}-D-lactoyl]]-L-alanyl-D-isoglutamine.

The compounds of the formula (I) may be prepared basically by the following method A or B.

Method A

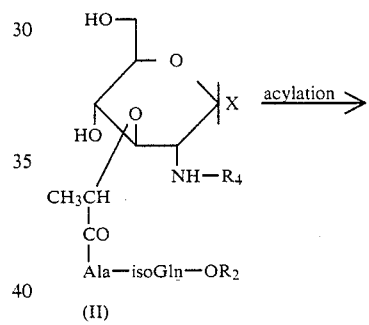

(II)

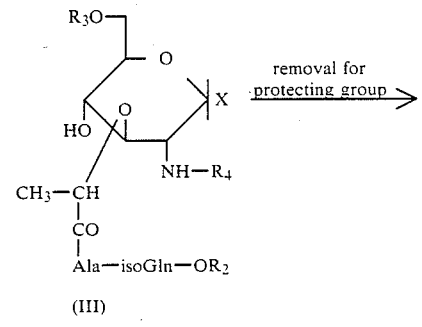

(III)

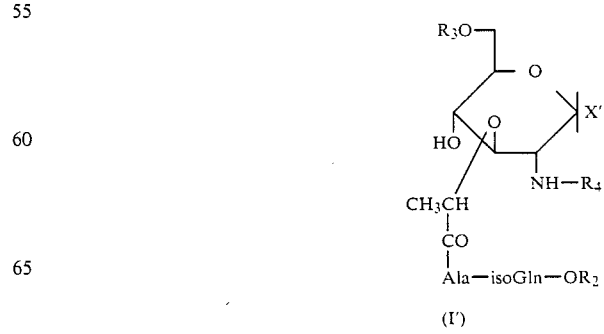

(I')

In the formulae, $R_2$, $R_3$ and $R_4$ have the same meanings as those in the formula (I), X is —OY or —SY (Y is a protecting group) and X' is hydroxy or mercapto group.

Method A consists of acylation step and step for removing a protecting group. The acylation step is conducted by reacting a compound of the formula (II) with an acylating agent ($R_3H$ or its reactive derivative). This step may be generally carried out in an anhydrous organic solvent such as dimethylformamide or dioxane at room temperature or a slightly elevated temperature. When $R_3H$ (free acid) as the acylating agent is used, the reaction is conducted in the presence of an appropriate condensing agent (e.g., N,N-dicyclohexylcarbodiimide, N-cyclohexyl-N'-morpholinolino-ethylcarbodiimide, N-cyclohexyl-N'-(4-diethylaminocyclohexyl)carbodiimide or N,N'-diethylcarbodiimide). As the reactive derivatives of $R_3H$ may be utilized conventional reactive derivatives used in the acylation such as mixed anhydrides, acid active esters or acid halides.

Protecting groups for protected hydroxy or mercapto group of X in the compound of the formula (II) are preferred to be easily removed under mild condition after the reaction. Examples of the protecting group are benzyl, phenacyl or trialkylsilyl (e.g., trimethylsilyl).

The removal for the protecting group may be generally conducted by solvolysis using water, alcohol or the like, or catalytic reduction in the presence of palladium catalyst, on which conventional conditions may be applied.

As the compounds of the formula (II), typical known compound is of $R_2$ being methyl, $R_4$ being acetyl and X being hydroxy. Other compounds (II) may be prepared in accordance with the method known for the above mentioned known compound and be utilized.

Furthermore, in the above method, it is desired to use the compound of the formula (II) wherein $R_2$ is a lower alkyl group. When the compound of the formula (IV) wherein $R_2$ is hydrogen atom is desired, it can be obtained by using the compound of the formula (II) wherein $R_2O$— is a protected hydroxy group (which can utilize the same protecting group for hydroxy group of X) and removing the protecting group after the acylation step.

Method B

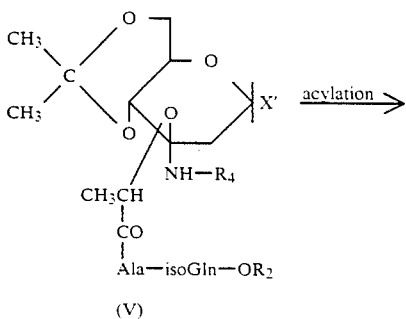

(V)

-continued
Method B

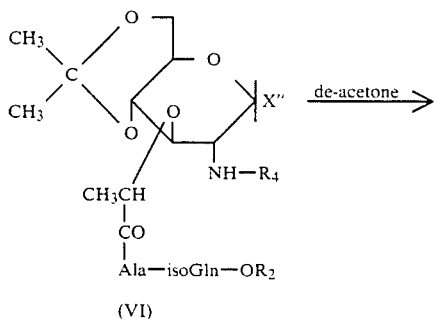

(VI)

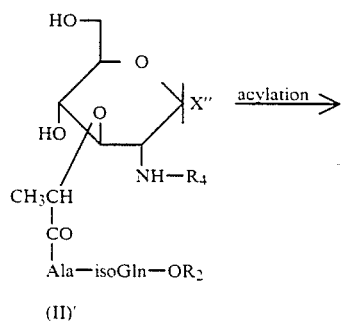

(II)'

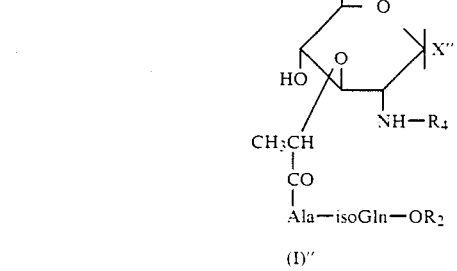

(I)''

In the above formulae, X' is hydroxy group or mercapto group and X'' is $C_{2-20}$alkanoyloxy or, $C_{2-20}$alkanoylthio, $R_3O$— or $R_3S$—, and $R_2$, $R_3$ and $R_4$ have the same meanings as those in the formula (I).

Method B consists of two kinds of acylation steps, i.e., acylations at 6th and 1st positions of the glucopyranose moiety, and de-acetone step.

The two kinds of acylation steps may be conducted under condition similar to that of the acylation step in Method A. The acylation step at 1st position of the glycopyranose moiety includes to use an acylating agent different from one in the acylation at 6th position ($C_{2-20}$alkane carboxylic acid or its reactive derivative).

The de-acetone step may be easily conducted by an acidic hydrolysis e.g., using 80% acetic acid aqueous solution at slightly elevated temperature.

Besides, the compounds of the formula (V) are known or may be easily prepared by known methods.

The compounds as obtained by the above methods may be purified in accordance with conventional methods such as column chromatography using alumina or silica gel, or recrystallization.

The compounds of the formula (I) possess activities for enhancing functions of cells relating to immune responses in the living bodies or for increasing numbers of the above cells and are useful as immunomodulators. Specifically, they may be, as immunomodulators, used for enhancing in vivo actions of vaccines such as BCG vaccines, hepatitis vaccines or influenza vaccines, various antibacterial agents or various antitumor agents.

The immunomodulator of this invention comprises a compound of the formula (I) and a pharmaceutically acceptable carrier. The immunomodulator may be an oral or parenteral form.

The oral form may be generally powders, tablets, emulsions, capsules, granules or liquids (including syrups). Examples of solid carriers for the oral form are lactose, starch, dextrin, calcium phosphate, calcium carbonate, synthetic or natural aluminum silicates, magnesium oxide, dry aluminum hydroxide, magnesium stearate, sodium hydrogen carbonate or dry yeast. Examples of liquid carriers for the oral form are water, glycerin or simple syrup.

The parenteral form is typically an injection. A carrier for the injection is generally sterilized distilled water. When the compound of the formula (I) is not easily soluble in water, an appropriate solubilizing agent is used.

Each of the preparations mentioned above may be prepared in accordance with conventional methods in the art.

The compound of the formula (I), when used for enhancing antitumour agents may be orally or parenterally administered generally in an amount of 150–250 μg/once a day for an adult. For enhancing vaccines, it may be generally administered in 0.5–2.0 mg/once in a week or two weeks for an adult. For enhancing hepatitis, it may be administered in a single dose of 0.5–2.0 mg/one or three times per three months. Further, for enhancing antibacterial agents it may be administered in 20–100 μg/once a day for an adult.

The compound of the formula (I) is generally formulated in itself together with an appropriate carrier, as mentioned above but may be formulated in combination with vaccines, antitumour agents or antibacterial agents to be strengthened.

Furthermore, the immunomodulator of this invention may be used for human being and also other mammals such as pig, cow, sheep, dog or cat.

EXAMPLE 1

N-[[2-O-{2-Acetamido-2,3-dideoxy-6-O-[(3R)-3-dodecanoyloxytetradecanoyl]-D-glucopyranos-3-yl}-D-lactoyl]]-L-alanyl-D-isoglutamine methyl ester:

A compound [(I): $R_1=C_6H_5CH_2O$, $R_2=CH_3$, $R_3=H$, $R_4=CH_3CO$], 150.0 mg was dissolved in 1 ml of dimethylformamide (DMF) and 1.5 ml of dioxane, to which 128.8 mg of (3R)-3-dodecanoyloxytetradecanoic acid, 15 mg of 4-dimethylaminopyridine (DMAP) and 78 mg of dicyclohexylcarbodiimide (DCC) were added and stirred for 16 hours at room temperature. After confirming the completion of reaction by a thin-layer chromatography ($CH_2Cl_2:CH_3OH=5:1$ v/v), 1 ml of methanol was added to the reaction mixture. The mixture was concentrated under reduced pressure to give a syrup. The syrup was subjected to a silica gel column chromatography [9 g of silica gel (Wako gel ®C 200) eluents of $CH_2Cl_2=MeOH$ v/v: (a) 150:1, (b) 70:1, (c) 40:1 and (d) 30:1]. The eluate (c) was concentrated under reduced pressure to obtain a syrup containing DMAP. The syrup was further purified by an alumina column chromatograph [eluents of $CH_2Cl_2$: MeOH v/v:(a) 100:1 and (b) 50:1] to afford 119.7 mg (47.3%) of the compound (I): $R_1=C_6H_5CH_2O$, $R_2=CH_3$, $R_3=(3R)$-3-dodecanoyloxytetradecanoyl, $R_4=CH_3CO$) having mp 153°–154.0° C.

A solution of 83.1 mg of the above mentioned compound in 2 ml of methanol and 1 ml of hexane was subjected to a catalytic hydrogenation using 100 mg of 10 % Pd-C for 4 days at room temperature. After confirming the completion of reaction by TLC ($CH_2Cl_2$: MeOH=6:1), the reaction mixture was filtered to remove the catalyst and washed with a mixture of dichloromethane and methanol (1:1). The combined filtrate and washing was concentrated under reduced pressure to afford 75.6 mg (quantitative) of the title compound.

Mp: 115°–116° C.
$[\alpha]^D$ (C=1.038, $CH_2Cl_2$: MeOH=1:1): +29.06°
IR λ max $cm^{-1}$(KBr): 3400, 2940, 2860, 1730, 1650, 1540.
Analysis for $C_{46}H_{82}N_4O_{14}$
Found (%): C 60.37; H 9.03; N 6.12.

EXAMPLE 2

N-[[2-O-{2-Acetamido-2,3-dideoxy-6-O-[(3R)-3-tetradecanoyloxytetradecanoyl]-D-glucopyranos-3-yl}-D-lactoyl]]-L-alanyl-D-isoglutamine methyl ester In using (3R)-3-tetradecanoyloxytetradecanoic acid instead of (3R)-3-decanoyloxytetradecanoic acid, example 1 was repeated to afford 117.2 mg of the title compound.

Mp: 115.0°–116.0° C.
$[\alpha]^D$ (C=1.038, $CH_2Cl_2$: MeOH=1:1): +26.95°
IR λ max $cm^{-1}$ (KBr) 3400, 2940, 2860, 1730, 1650, 1540.
Analysis for $C_{48}H_{86}N_4O_{14}$
Found (%): C 61.12; H 9.18; N 5.94.
NMR ($CDCl_3$-$CD_3OD$), δ(ppm): 0.88(t,6H,J=6.6 Hz), 1.25–1.58(m,42H), 1.38(d,3H,J=6.6 Hz), 1.40(d,3H,J=7.0 Hz), 1.98(s,3H), 2.28(t,2H,J=7.7 Hz), 2.44–2.61(m,4H), 3.69(s,3H), 5.76(m,1H), 5.34(d,1H,J=2.6 Hz).

EXAMPLE 3

N-[[2-O-{2-Acetamido-2,3-dideoxy-6-O-[(3R)-3-hexadecanoyloytetradecanoyl]-D-glucopyranos-3-yl}-D-lactoyl]]-L-alanyl-D-isoglutamine methyl ester:

In using 194.4 mg of (3R)-3-hexadecanoyloxytetradecanoic acid instead of (3R)-3-dodecanoyloxytetradecanoic acid and 200.0 mg of the compound [(I): $R_1=C_6H_5CH_2O$, $R_2=CH_3$, $R_3=H$, $R_4=CH_3CO$], example 1 was repeated to afford 147.7 mg (41.5 %) of the (3R)-3-hexadecanoyloxytetradecanoyl compound as intermediate and 105.0 mg of the title compound.

Mp: 115.0°–116° C.
$[\alpha]^D$ (C=0.864, $CH_2CH_2$:MeOH=1:1): +25 95°
IR λ max $cm^{-1}$ (KBr): 3400, 2940, 2860, 1730, 1600, 1540.
Analysis for $C_{50}H_{90}N_4O_{14}$
Found (%): C 61.83; H 9.33; N 5.77.
NMR ($CDCl_3$-$CD_3OD$), δ(ppm): 0.88(t,6H,J=6.6 Mz), 1.25–1.58(m,46H), 1.38(d,3H,J=6.6 Hz), 1.40(d,3H,7.0 Hz), 1.98(s,3H), 2.28(t,2H,J=7.5 Hz) 2.44–2.61(m,4H), 3.69(s,3H), 5.26(m,1H), 5.35(d,1H,J=2.9 Hz).

EXAMPLE 4

N-[[2-O-{2-Acetamido-1,5-anhydro-2,3-dideoxy-6-O-[(3R)-3-dodecanoyloxytetradecanoyl-D-glucitol-3-yl}-D-lactoyl]-L-alanyl-D-isoglutamine methyl ester:

A compound [(I): $R_1=H$, $R_2=CH_3$, $R_3=H$, $R_4=CH_3CO$] 150 mg was dissolved in 1 mg of DMF under warming, to which 144.9 mg of (3R)-3-dodecanoyloxytetradecanoic acid, 17 mg of DMAP and 117 mg of DCC were added and stirred for 24 hours at room temperature. After completing the reaction, the mixture was subjected to a silica gel chromatography eluents of $CH_2Cl_2$: MeOH=(a) 150:1, (b) 60:1, (c) 40:1 and (d) 30:1] and the eluate (c) was concentrated under reduced pressure to obtain a syrup remaining DMAP. The syrup was subjected an alumina chromatography using eluents of $CH_2CH_2$:MeOH being (a) 100:1 and (b) 50:1. The title compound, 85.8 mg (33.7 %) was obtained from the eluate (b).

Mp: 128.0°–129.0° C.

$[\alpha]^D$ (C=1.232, $CH_2Cl_2$: MeOH=1:1): +15.58°

IR λ max $cm^{-1}$ (KBr) 3300, 2940, 2860, 1740, 1660, 1550.

Analysis for $C_{46}H_{82}N_4O_{13}$

Found (%): C 61.44; H 9.19; N 6.23.

NMR ($CDCl_3$-$CD_3OD$), δ(ppm): 0.88(t,6H,J=6.6 Hz), 1.26–1.59(m,38H), 1.38(d,3H,J=5.9 Hz), 1.40(d,3H,J=6.6 Hz), 1.96(s,3H), 2.28(t,2H,J=7.5 Hz), 2.42–2.62(m,4H), 3.06(t,1H,J=11.0 Hz), 3.69(s,3H), 4.17(dd,1H,J=11.0,5.1 Hz), 5.24(m,1H).

EXAMPLE 5

N-[[2-O-{2-Acetamido-1,5-anhydro-2,3-dideoxy-6-O-[(3R)-3-tetradodecanoyloxytetradecanoyl]-D-glucitol-3-yl}-D-lactoyl]]-L-alanyl-D-isoglutamine methyl ester:

In using (3R)-3-tetradecanoyloxytetradecanoic acid instead of (3R)-3-dodecanoyloxytetradecanoic acid, example 4 was repeated to afford 117.3 mg (44.6%) of the title compound.

Mp: 128.0°–129° C.

$[\alpha]^D$ (C=1.005, $CH_2Cl_2$: MeOH: 1:1): +14.62°

IR λ max $cm^{-1}$ (film) 3400, 3300, 2940, 2860, 1740, 1640, 1550.

Analysis for $C_{48}H_{86}N_4O_{13}$

Found (%): C 62.17; H 9.34; N 6.04.

NMR ($CDCl_3$-$CD_3OD$), δ (ppm) 0.88(t,6H,J=6.6 Hz), 1.26–1.59(m,42H), 1.38(d,3H,J=6.2 Hz), 1.40(d,3H, J=6.2 Hz), 1.96(s,3H), 2.28(t,2H,J=7.7 Hz), 2.42–2.62(m,4H), 3.06(t,1H,J=11.0 Hz), 3.69(s,3H), 4.16(dd,1H,J=11.0,5.1 Hz), 5.24(m,1H).

EXAMPLE 6

N-[2-O-{2-Acetamido-1,5-anhydro-2,3-dideoxy-6-O-[(3R)-3-hexadecanoyloxytetradecanoyl]-D-glusitol-3-yl}-D-lactoyl]]-L-alanyl-D-isoglutamine methyl ester:

In using 164.0 mg of (3R)-3-hexadecanoyloxytetradecanoic acid instead of (3R)-3-dodecanoyloxytetradecanoic acid, example 4 was repeated to afford 100.1 mg of the title compound.

Mp: 128°–129° C.

$[\alpha]^D$ (C=0.818, $CH_2Cl_2$: MeOH=1:1): +13.81°

IR λ max $cm^{-1}$ (film) 3400, 3300, 2940, 2850, 1740, 1650, 1540.

NMR ($CDCl_3$-$CD_3OD$), δ(ppm): 0.88(t,6H,J=5.7 Hz), 1.26–1.60(m,46H), 1.38(d,3H,J=6.2 Hz), 1.40(d,3H,J=6.2 Hz), 1.96(s,3H), 2.28(t,2H,J=7.3 Hz), 2.44–2.62(m,4H), 3.69(s,3H), 4.15(dd,1H,J=11.4, 5.1 Hz), 5.24(m,1H).

EXAMPLE 7

N-[[2-O-{2-Acetamido-2,3-dideoxy-6-O-[(3R)-3-dodecanoyloxytetradecanoyl]-1-thio-β-D-glucopyranos-3-yl}-D-lactoyl]]-L-alanyl-D-isoglutamine methyl ester:

To a solution of 200.0 mg of a compound [(I): $R_1=SCOCH_3$, $R_2=CH_3$, $R_3=H$, $R_4=CH_3CO$] in 1 ml of DMF and 1.5 ml of dioxane were added 181.3 mg of (3R)-3-dodecanoyloxytetradecanoic acid, 22 mg of DMAP and 146 mg of DCC, followed by stirring for 3 hours at room temperature. After completing the reaction, 1 ml of methanol was added to the reaction mixture and the mixture was concentrated under reduced pressure. The resulting syrup was subjected to a silica gel chromatography [eluents of $CH_2Cl_2$: MeOH=(a) 150:1, (b) 60:1, (c) 40:1 and (d) 30:1]. The eluate (c) was concentrated under reduced pressure to obtain syrup remaining DMAP. The syrup was further purified through an alumina chromatography [eluents of $CH_2Cl_2$: MeOH=(a) 100:1, (b) 50:1]. The title compound, 6.9 mg (28.6%) was obtained from the eluate (b).

Mp: 102.0°–103.0° C.

$[\alpha]^D$ (C=0.960, $CH_2Cl_2$: MeOH=1:1): +8.75°

IR λ max $cm^{-1}$ (film): 3300, 2940, 2860, 2550, 1740, 1660, 1540.

Analysis for $C_{46}H_{82}N_4O_{13}S$

Found (%): C 59.33; H 8.87; N 6.02.

NMR ($CDCl_3$-$CD_3OD$), δ(ppm): 0.88(t,6H,J=6.4 Hz), 1.26–1.60(m,38H), 1.36(d,3H,J=7.0 Hz), 1.42(d,3H,J=7.3 Hz), 1.96(s,3H), 2.30(t,2H,J=7.5 Hz), 2.36–2.64(m,4H), 3.70(s,3H), 4.48(d,1H,J=9.9 Hz), 5.25(m,1H).

EXAMPLE 8

N-[[2-O- {2-Acetamido-2,3-dideoxy-6-O-[(3R)-3-tetradecanoyloxytetradecanoyl]-1-thio-β-D-glucopyranos-3-yl}-D-lactoyl]]-L-alanyl-D-isoglutamine methyl ester:

In using 193.2 mg of (3R)-3-tetradecanoyloxytetradecanoic acid instead of (3R)-3-dodecanoyloxytetradecanoic acid, example 7 was repeated to afford 111.4 mg (31.9%) of the title compound.

Mp: 102.0°–103.0° C.

$[\alpha]^D$ (C=1.294, $CH_2Cl_2$: MeOH=1:1): +8.19°IR λ max $cm^{-1}$ (film): 3400, 3300, 2940, 2860, 2550, 1740, 1660, 1540.

Analysis for $C_{48}H_{86}N_4O_{13}S$

Found (%): C 60.09; H 9.03; N 5.84.

NMR ($CDCl_3$-$CD_3OD$), δ(ppm): 0.88(t,6H,J=6.6 Hz), 1.26–1.60(m,42H), 1.36( ,3H,J=7.0 Hz), 1.42(d,3H,J=7.0 Hz), 1.97(s,3H), 2.30(t,2H,J=7.6 Hz), 2.42–2.62(m,4H), 3.70(s,3H), 4.50(d,1H,J=9.9 Hz), 5.25(m,1H).

EXAMPLE 9

N-[[2-O-{2-Acetamido-2,3-dideoxy-6-O-[(3R)-3-hexadodecanoyloxytetradecanoyl]-1-thio-β-D-glucopyranos-3-yl}-D-lactoyl]]-L-alanyl-D-isoglutamine methyl ester:

In using 205.1 mg of (3R)-3-hexadecanoyloxytetradecanoic acid instead of (3R)-3-dodecanoyloxytetradecanoic acid, example 7 was repeated to afford 106.6 mg of the title compound.

Mp: 102.0°–103.0° C.

$[\alpha]^D$ (C=1.066, $CH_2Cl_2$: MeOH=1:1): +7.58°

IR λ max $cm^{-1}$ (film) 3400, 3300, 2940, 2860, 2550, 1740, 1640, 1540.

Analysis for $C_{50}H_{90}N_4O_{13}S$

Found (%): C 60.82; H 9.18; N 5.67.

According to one aspect of the invention, it provides a method for treating a patient suffering immune depression due to tumors or hepatitis which comprises administering to the patient an immunomodulator of the invention and an antitumor agent or antihepatitic agent, simultaneously or separately. It also provides a method for preventing infection of influenza virus to human being which comprises administering to the human being an immunomodulator of the invention and a vaccine for influenza virus, simultaneously or separately.

Next, pharmacological activities on typical compounds of the invention are shown as follows.

(1) Enhancing action on BCG vaccine (adjuvant activity)

0.2 ml of an equivalent weight mixture of a solution of BCG killed vaccine in physiological saline (100 μg/ml) and a solution of a compound of the invention in Freund's incomplete adjuvant (1000 μg/ml) was subcutaneously injected to the back of ICR mouse (one group consisting of 7 mice). After 14 days, 10 μg of tuberculin was intradermally injected into the hind foot-pad. Swelling of the foot-pad was measured after 24 hours (24 hours foot-pad test).

The control is the above mentioned mixture excluded a compound of the invention.

The results of the foot-pad test are shown in Table.

| Test Compound | Swelling of Foot-pad (× 0.01 mm) |
|---|---|
| Example 1 | 59.2 ± 15.1 |
| 2 | 57.4 ± 16.3 |
| 3 | 66.2 ± 12.3 |
| 4 | 78.6 ± 19.1 |
| 5 | 69.3 ± 18.8 |
| 6 | 86.4 ± 22.1 |
| 7 | 50.6 ± 13.6 |
| 8 | 51.8 ± 11.0 |
| 9 | 49.1 ± 12.0 |
| Control | 46.0 ± 16.5 |

(2) Enhancing effect on hepatitis vaccine (adjuvant activity)

A compound of the invention was dissolved or suspended in physiological saline (100 μg/ml), and mixed with a solution of B type hepatitis vaccine (HBs) in physiological saline (100 μg/m) at an equivalent weight ratio to obtain the test solution. A solution excluded the compound of the invention from the test solution was used as control.

The test solution (0.2 ml) was intraperitoneally injected into $CDF_1$ mouse (one group consisting of 10 mice). At 3 weeks after the administration, a blood was taken from the intravenous vein in eyeground of each the mice and centrifuged to obtain serum (primary response serum). Further, 0.2 ml of the test solution was again intraperitoneally injected into each mice, and at 2 weeks stage, serum was separated in the similar way (secondary response serum).

Value for IgG antibody against B type hepatitis virus of the resulting serum was measured by ELISA method.

The results are shown in Table.

| Test Compound | Anti HBs-ELISA unit | |
|---|---|---|
| | Primary response serum | Secondary response serum |
| Example 1 | 10,800 | 150,000 |
| 2 | 6,000 | 195,000 |
| 3 | 24,000 | 575,000 |
| 4 | 5,200 | 175,000 |
| 5 | 3,600 | 120,000 |
| 6 | 6,200 | 220,000 |
| 7 | 2,500 | 110,000 |
| 8 | 2,200 | 105,000 |
| 9 | 3,400 | 150,000 |
| Control | 1,500 | 30,000 |

(3) Enhancing effect on influenza HA vaccine (adjuvant activity)

A compound of the invention was dissolved or suspended in physiological saline (100 μg/ml). Separately, influenza HA vaccine (A/Bangkok/10/83 strain, H1N1) was dissolved in physiological saline (100 CCA/ml). These two solutions were mixed in an equivalent weight to make the test solution. Control is a solution excluded the compound of the invention from the test solution.

The test solution was administered into $CDF_1$ mouse in a similar way to that of the test of enhancing action for hepatitis vaccine as mentioned above, to obtain primary and secondary response sera.

The results are as in Table

| Test compound | Anti-influenza HA virus ELISA unit | |
|---|---|---|
| | Primary response serum | Secondary response serum |
| Example 1 | 4,800 | 34,000 |
| 2 | 3,100 | 33,000 |
| 3 | 5,200 | 57,000 |
| 4 | 2,300 | 32,000 |
| 5 | 1,800 | 28,000 |
| 6 | 2,500 | 30,000 |
| 7 | 2,000 | 26,000 |
| 8 | 2,100 | 22,000 |
| 9 | 1,900 | 25,000 |
| Control | 1,100 | 8,300 |

(4) Activation for macrophages

A test solution of a compound of the invention in physicological saline (500 μg/ml, 0.2 ml) was intraperioneally injected into $CDF_1$ mouse (one group consisting of mice). Intraperioneal macrophages which were collected after 4 days and leukemia cells of L-1210 mouse were mixed at the cell ratio of 20 and 1. Each 200 μl of the mixture was put on a microplate having 96 holes. After 72 hours, numbers of cells in each holes were counted, and cytostatic rate of the mixture was measured.

| Test compound | Cytostatic rate (%) |
|---|---|
| Example 1 | 40.0 ± 1.2 |
| 2 | 45.2 ± 1.1 |
| 3 | 22.3 ± 1.0 |
| 4 | 55.2 ± 2.8 |
| 5 | 58.6 ± 2.9 |
| 6 | 42.6 ± 3.2 |
| 7 | 22.8 ± 2.6 |
| 8 | 31.6 ± 1.6 |
| 9 | 38.2 ± 2.2 |
| Control (saline) | 5.8 ± 0.8 |

(5) Stimulation effect on anti-body precluding cells

A solution of sheep leukocytes (SRBC) in phosphate buffered physiological saline (5×10⁷ cells/ml), 0.2 ml was injected into tail intravenous vein of ICR mouse (7 mice per group). At the same time, a solution of a compound of the invention in physiological saline (500 μg/ml), 0.2 ml was similarly injected. After 4 days, lien was picked up from the treated mouse to obtain splenic cells. Plaque numbers were measured by Cunningham technique.

The results are shown in Table.

| Test compound | Plaque No. (× 10³) | Stimulation index |
|---|---|---|
| Example 1 | 10.56 ± 8.3 | 2.2 |
| 2 | 8.23 ± 7.2 | 1.7 |
| 3 | 21.23 ± 9.9 | 4.4 |
| 4 | 6.67 ± 3.6 | 1.4 |
| 5 | 5.83 ± 3.2 | 1.2 |
| 6 | 6.81 ± 4.8 | 1.4 |
| 7 | 10.88 ± 9.8 | 2.3 |
| 8 | 8.63 ± 7.9 | 1.8 |
| 9 | 11.00 ± 10.1 | 2.3 |
| Control (saline) | 4.78 ± 2.46 | 1 |

(6) Phylactic effect

A solution of a compound of the invention in physiological saline (500 μg/ml), 0.2 ml was intraperitoneally injected into ICR mouse (20 mice per group). After a day, *E. coli* (JC-2) and *Psud. aeruginosa* (NCTC 10490) were incubated through intraperitoneal route so as to be at concentration of 1×10⁷/mouse. Survival rate after 7 days of infection was measured.

| Test compound | Survival rate % | |
|---|---|---|
| | E. coli | Psud. aeruginosa |
| Example 1 | 50 | 45 |
| 2 | 55 | 45 |
| 3 | 45 | 40 |
| 4 | 65 | 50 |
| 5 | 70 | 55 |
| 6 | 60 | 50 |
| 7 | 30 | 20 |
| 8 | 35 | 20 |
| 9 | 40 | 15 |
| Control (saline) | 0 | 5 |

(7) Antitumour effect

Meth A fibrosarcomas were suspended in phosphate buffered physiological saline (1×10⁶ cells/ml). Separately, a solution of a compound of the invention in physiological saline was prepared (1,000 μg/ml). An equivalent weight mixture of these two solution (0.2 ml) was subcutaneously injected into BALB/C mouse (20 mice per group). Survival rate after 35 days was measured.

The results are shown in Table.

| Test compound | Survival rate (%) |
|---|---|
| Example 1 | 30 |
| 2 | 30 |
| 3 | 20 |
| 4 | 35 |
| 5 | 35 |
| 6 | 30 |
| 7 | 10 |
| 8 | 5 |
| 9 | 5 |
| Control | 0 |

What we claim is:

1. A muramyl peptide derivative having the formula (I):

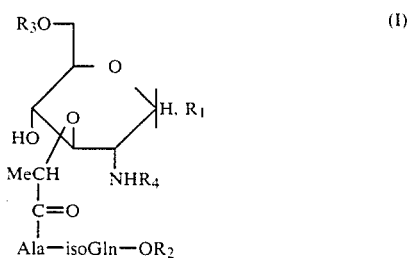

in which "Ala" is

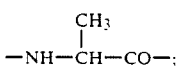

"iso-Gln" is

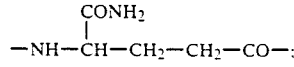

$R_1$ is hydrogen atom, hydroxy group, mercapto group, a $C_{2-20}$alkanoyloxy group, a $C_{2-20}$alkanoylthio group, $R_3O-$ or $R_3S-$; $R_2$ is hydrogen atom or a $C_{1-20}$alkyl group, $R_3$ is a group the sub-formula:

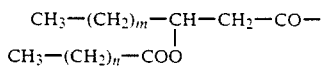

($n$ is an integer of 10–14 and $m$ is an integer of 8–12); and $R_4$ is a $C_{2-4}$alkanoyl group.

2. A compound of claim 1 wherein $R_3$ is 3-dodecanoyloxytetradecanoyl or 3-hexadecanoyloxytetradecanoyl group.

3. A compound of claim 1 wherein $R_1$ is hydrogen atom or hydroxy group.

4. A compound of claim 1 wherein $R_4$ is acetyl group.

5. A compound of claim 1 wherein $R_2$ is hydrogen atom or methyl group.

6. A compound of claim 1 wherein "Ala" is a residue of L-alanine and "iso-Gln" is a residue derived from D-isoglutamine.

7. A compound of claim 1 which is
N-[[2-O-{2-acetamido-2,3-dideoxy-6-O-[(3R)-3-dodecanoyloxytetraecanoyl]-D-glucopyranos-3-yl}-D-lactoyl]]-L-alanyl-D-isoglutamine methyl ester,
N-[[2-O-{2-acetamido-2,3-dideoxy-6-O-[(3R)-3-tetradecanoyloxytetradecanoyl]-D-glucopyranos-3-yl}-D-lactoyl]]-L-alanyl-D-isoglutamine methyl ester,
N-[[2-O-{2-acetamido-2,3-dideoxy-6-O-[(3R)-3-hexadecanoyloxytetradecanoyl]-D-glucopyranos-3-yl}-D-lactoyl]]-L-alanyl-D-isoglutamine methyl ester,
N-[[2-O-{2-acetamido-1,5-anhydro-2,3-dideoxy-6-O-[(3R)-3-dodecanoyloxytetradecanoyl-D-glucitol-3-yl}-D-lactoyl]]-L-alanyl-D-isoglutamine methyl ester,
N-[[2-O-{2-acetamido-1,5-anhydro-2,3-dideoxy-6-O-[(3R)-3-tetradecanoyloxytetradecanoyl]-D- glucitol-3-yl}-D-lactoyl]]-L-alanyl-D-isoglutamine methyl ester,

N-[[2-O-{2-acetamido-1,5-anhydro-2,3-dideoxy-6-O-(3R)-3-hexadecanoyloxytetradecanoyl]-D-glucitol-3-yl}-D-lactoyl]]-L-alanyl-D-isoglutamine methyl ester, N-[[2-O-{2-acetamido-2,3-dideoxy-6-O-[(3R)-3-dodecanoyloxytetradecanoyl]-1-thio-β-D-glucopyranos-3-yl}-D-lactoyl]]-L-alanyl-D-isoglutamine methyl ester or N-[[2-O-{2-acetamido-2,3-dideoxy-6-O-[(3R)-3-tetradecanoyloxytetradecanoyl]-1-thio-β-D-glucopyranos-3-yl}-D-lactoyl]]-L-alanyl-D-isoglutamine methyl ester.

8. An immunomodulator composition which comprises a compound of claim 1 and a pharmaceutically acceptable carrier.

9. An immunomodulator composition which comprises a compound of claim 1 which is used to enhance activities in the living body of BCG, hepatitis, or influenza virus vaccines.

10. An immunomodulator composition which comprises a compound of claim 1 which is used to enhance activities in the living body of antibacterial agents.

11. An immunomodulator composition which comprises a compound of claim 1 which is used to enhance activities in the living body of antitumor agents.

12. An immunomodulator composition which comprises a compound of claim 2 and a pharmaceutically acceptable carrier.

13. An immunomodulator composition which comprises a compound of claim 3 and a pharmaceutically acceptable carrier.

14. An immunomodulator composition which comprises a compound of claim 4 and a pharmaceutically acceptable carrier.

15. An immunomodulator composition which comprises a compound of claim 5 and a pharmaceutically acceptable carrier.

16. An immunomodulator composition which comprises a compound of claim 6 and a pharmaceutically acceptable carrier.

17. An immunomodulator composition which comprises a compound of claim 7 and a pharmaceutically acceptable carrier.

* * * * *